(12) United States Patent
Vanmoor

(10) Patent No.: US 6,436,995 B1
(45) Date of Patent: Aug. 20, 2002

(54) METHOD OF TREATING HEADACHES BY ENHANCING THE EFFECTIVENESS OF THE HUMAN IMMUNE SYSTEM

(76) Inventor: Arthur Vanmoor, 22 SE. 4 St., Boca Raton, FL (US) 33432-6016

( * ) Notice: Subject to any disclaimer, the term of this patent is extended or adjusted under 35 U.S.C. 154(b) by 0 days.

(21) Appl. No.: 09/717,633

(22) Filed: Nov. 21, 2000

(51) Int. Cl.$^7$ .............................................. A61K 31/195
(52) U.S. Cl. ...................................................... 514/562
(58) Field of Search .................. 514/562, 563

(56) References Cited

U.S. PATENT DOCUMENTS 5,707,967 A * 1/1998 Vanmoor .................... 514/562

* cited by examiner

Primary Examiner—Phyllis G. Spivack
(74) Attorney, Agent, or Firm—Otto S Kauder

(57) ABSTRACT

There is disclosed a method of treating a headache, particularly a migraine in a person in need of such treatment, which comprises enhancing the effectiveness of the person's immune system by the administration to such person of at least one aliphatic sulfur compound, preferably a sulfur-containing amino-acid derivative having the formula (I)

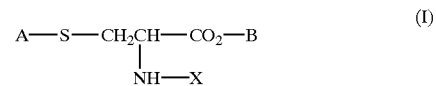

in which A is hydrogen or a carboxymethylene —$CH_2CO_2H$ group, B is hydrogen or an alkyl group having 1 to 3 carbon atoms, and X is an acyl group —CO—R in which R is an alkyl group having 1 to 3 carbon atoms, or a pharmaceutically acceptable salt of such compound.

18 Claims, No Drawings

METHOD OF TREATING HEADACHES BY ENHANCING THE EFFECTIVENESS OF THE HUMAN IMMUNE SYSTEM

BACKGROUND OF THE INVENTION

1. Field of the Invention.

This invention relates to a method of treating a person suffering from headaches, in particular a migraine condition, with an agent that enhances the effectiveness of the human immune system to mitigate and where possible eliminate the migraine.

2. Description of Related Art.

Most headache conditions are self-medicated by the victims with non-steroidal anti-inflammatory remedies such as aspirin, acetaminophen, and ibuprofen.

Migraine is a distinctive kind of headache condition marked by much greater intensity and duration than other headaches, and also is much less likely to respond favorably to the common remedies. See, for example, "Health Journal" by T. Parker-Pope, Wall Street Journal, May 5, 2000.

As is well known, the search for better remedies for migraine and other headache conditions is enormously costly. For economic reasons, moreover, the search tends to be skewed in the direction of finding novel remedies proprietary to their discoverers and owners. Novel remedies, of course, come into being with nothing known about either their safety or their effectiveness, so that both of these essential attributes need to be exhaustively studied before they can be used as intended. For a summary of how this has been accomplished in the art reference can be had to U.S. Pat. No. 5,707,967 here incorporated by reference.

In contrast, the art has tended to neglect the exploration of therapeutic properties of known substances that humans have been safely ingesting for untold generations. Along these lines, the present inventor has been able to bring about in susceptible individuals within a limited and reproducible time the appearance of headache by administering selected foods and food ingredients as trigger substances, and to use these as research tools to study the effectiveness of certain nutrient substances in relieving these artificially produced conditions as well as their natural counterparts. As a result, certain water soluble amino carboxylic acid compounds are disclosed in U.S. Pat. No. 5,707,967 as effective against headache.

Stroppolo et al U.S. Pat. No. 5,500,226 disclosed a pharmaceutical composition for oral use having analgesic activity containing a mixture of arginine and (S)-Ibuprofen in a molar ratio between 1.1 and 1.9.

SUMMARY OF THE INVENTION

In accordance with this invention, there is provided a method of treating in a person in need thereof a headache, and particularly a migraine condition,, which comprises the administration to such person of at least one aliphatic sulfur compound. The beneficial effect of administering aliphatic sulfur compound is believed to accompany an enhancement of the effectiveness of the person's immune system.

The aliphatic sulfur compound preferably includes a sulfur-methylene moiety such as —SCH$_2$— or —SCH$_2$CH—

More preferably, the aliphatic sulfur compound also includes a carboxyl group, as in

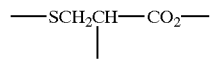

Still more preferably, the aliphatic sulfur compound is a sulfur-containing amino-acid derivative of an ethyl sulfide having the formula (I)

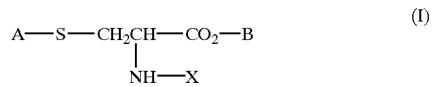

(I)

in which A is hydrogen or a carboxymethylene —CH$_2$CO$_2$H group, B is hydrogen or an alkyl group having 1 to 3 carbon atoms, and X is hydrogen, or an acyl group —CO—R in which R is an alkyl group having 1 to 3 carbon atoms, or a pharmaceutically acceptable salt of such compound.

In this compound, the ethyl sulfide group

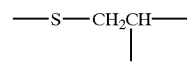

is believed to be responsible for the beneficial activity observed while the attached groups A, —NHX, and —CO$_2$B assist in delivering the compound to the site within the human organism where the beneficial activity is exerted.

In one preferred embodiment, A is hydrogen.

In a further preferred embodiment, A, B, and X are not simultaneously hydrogen.

Particularly suitable illustrative derivatives having the formula given above are tabulated by showing the assignments of A, B, and X in the above formula:

| Compound | A | B | X |
|---|---|---|---|
| 1 | —CH$_2$CO$_2$H | H | H |
| 2 | H | H | COCH$_3$ |
| 3 | H | CH$_3$ | H.HCl |
| 4 | H | C$_2$H$_5$ | H.HCl |
| 5 | H | H | H |
| 6 | H | H | H.HCl |

The present invention is based on the recognition that enhancing the effectiveness of the immune system in a person can be beneficial in augmenting the person's innate ability to resist the initiation and intensification of migraine conditions and other headaches, as well as the uncomfortable after-effects. Consequently, the quality of life is improved.

In increasing the effectiveness of the human immune system according to this invention, mega-nutrient doses of 2 to 20 grams of a compound or compounds of formula (I) can be administered to a person experiencing or fearful of the occurrence of migraine to diminish its extent and duration. Doses can be administered in any convenient manner, as by oral administration in any of the usual dosage forms, such as tablets, capsules, solutions, and dispersions in liquid foods such as soups and fruit juices. Alternatively, there can be given sterile solutions by direct injection into the bloodstream of the person to be treated, as well as by rectal suppositories.

EXAMPLE 1

A female volunteer with a long history of severe periodic migraine was given ten grams of composition comprising several compounds of formula (I) as soon as she felt the pain approaching, and repeated at intervals of 3–4 hours until the pain ceased. She then reduced the dose to ten grams per day and has not had a recurrence of migraine.

What is claimed is:

1. A method of treating a headache in a person in need of such treatment, which comprises the administration to such person of at least one sulfur-containing amino-acid derivative having the formula (I)

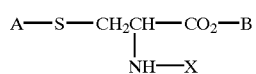
(I)

in which A is hydrogen or a carboxymethylene —$CH_2CO_2H$ group, B is hydrogen or an alkyl group having 1 to 3 carbon atoms, and X is an acyl group —CO—R in which R is an alkyl group having 1 to 3 carbon atoms, or a pharmaceutically acceptable salt of such compound.

2. The method of claim 1, wherein the headache condition is migraine.

3. The method of claim 1, wherein A is hydrogen or a carboxymethylene group —$CH_2CO_2H$.

4. The method of claim 1, wherein B is H or an alkyl group having 1 to 3 carbon atoms.

5. The method of claim 1, wherein said amino-acid derivative is administered orally with food.

6. The method of claim 1, wherein said amino-acid derivative is administered orally prior to or simultaneously with perception of a headache.

7. The method of claim 1, wherein said amino-acid derivative is administered by injection into the bloodstream.

8. The method of claim 1, wherein said amino-acid derivative is administered by rectal suppository.

9. The method of claim 1, wherein said amino-acid derivative is administered in one to eight daily doses of 2 to 20 grams each.

10. The method of claim 1, wherein the total of said amino-acid derivative administered daily is in the range of 10 to 50 grams.

11. The method of claim 1, wherein said amino-acid derivative is the compound of formula (I) in which A is H, B is H, and X is $COCH_3$.

12. The method of claim 1, wherein said person experiences relief from the effects of said headache.

13. The method of claim 1, wherein after treatment said headache is not observed.

14. The method of claim 1, wherein a plurality of compounds having formula (I) is administered.

15. A method of treating a headache in a person in need of such treatment, which comprises enhancing the effectiveness of the person's immune system by the administration to such person of at least one sulfur-containing amino-acid derivative having the formula (I)

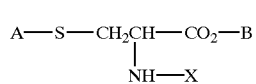
(I)

in which A is hydrogen or a carboxymethylene —$CH_2CO_2H$ group, B is hydrogen or an alkyl group having 1 to 3 carbon atoms, and X an acyl group —CO—R in which R is an alkyl group having 1 to 3 carbon atoms, or a pharmaceutically acceptable salt of such compound.

16. The method of claim 15, wherein in a plurality of compounds having formula (I) is administered.

17. The method of claim 15, wherein said amino-acid derivative is administered with food.

18. The method of claim 15, wherein said amino-acid derivative is administered in one to eight daily doses of 2 to 20 grams each.

* * * * *